United States Patent
Shain et al.

(10) Patent No.: US 6,569,157 B1
(45) Date of Patent: May 27, 2003

(54) REMOVAL OF STRATUM CORNEUM BY MEANS OF LIGHT

(75) Inventors: Eric B. Shain, Glencoe, IL (US); Mark R. Pope, Grayslake, IL (US); Joseph L. Pezzaniti, Round Lake, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/080,432

(22) Filed: May 18, 1998

(51) Int. Cl.[7] .............................................. A61B 18/20
(52) U.S. Cl. .............................. 606/12; 606/9; 606/10; 606/13
(58) Field of Search ................................ 606/9–12, 13

(56) References Cited

U.S. PATENT DOCUMENTS

| | | |
|---|---|---|
| 3,871,772 A | 3/1975 | Munnerlyn et al. |
| 4,015,906 A | 4/1977 | Sharon |
| 4,213,704 A | 7/1980 | Burns et al. |
| 4,622,971 A | 11/1986 | Yamamoto et al. |
| 4,668,088 A | 5/1987 | Quinque et al. |
| 4,775,361 A | * 10/1988 | Jacques et al. |
| 5,165,418 A | * 11/1992 | Tankovich et al. |
| 5,374,556 A | * 12/1994 | Bennett et al. |
| 5,423,803 A | * 6/1995 | Tankovich et al. |

FOREIGN PATENT DOCUMENTS

| | | |
|---|---|---|
| DE | 39 34 640 | 2/1991 |
| WO | 9409713 | * 5/1994 |

* cited by examiner

Primary Examiner—David M. Shay
(74) Attorney, Agent, or Firm—David L. Weinstein

(57) ABSTRACT

The invention involves a method for focusing light comprising the steps of: projecting at least one pulse of light onto the surface of the skin of a patient; collecting at least a portion of the light that is reflected from the skin of the patient; projecting the collected, reflected light onto a detector; and adjusting the projection of the pulsed light onto the surface of the skin of the patient in such a manner that the signal projected onto the detector is optimized. When the light pulse is properly focused, e.g., when it is characterized by the best focus, it can be used to provide energy to form an opening in the skin of the patient. When more than one pulse of light is required to form an opening in the skin of the patient, aligning the light prior to each pulse will improve the efficiency of formation of the opening. In general, the method for aligning and focussing is the same as the method for focusing, with the difference being that aligning further includes steps for moving the spot of light formed by the light so that it strikes the surface of the skin at or near the position on the surface of the skin of the patient at which the previous spot of light struck the skin.

26 Claims, 4 Drawing Sheets

REMOVAL OF STRATUM CORNEUM BY MEANS OF LIGHT

BACKGROUND OF THE INVENTION

1. Field of the Invention

This invention relates to a method and apparatus for forming an opening in the skin for the purpose of providing access to biological fluids for determining the concentration of analytes in the biological fluids.

2. Discussion of the Art

The prevalence of diabetes has been increasing markedly in the world. At this time, diagnosed diabetics represented about 3% of the population of the United States. It is believed that the total actual number of diabetics in the United States is over 16,000,000. Diabetes can lead to numerous complications, such as, for example, retinopathy, nephropathy, and neuropathy.

The most important factor for reducing diabetes-associated complications is the maintenance of an appropriate level of glucose in the blood stream. The maintenance of the appropriate level of glucose in the blood stream may prevent and even reverse many of the effects of diabetes.

Glucose monitoring devices of the prior art have operated on the principle of taking blood from an individual by a variety of methods, such as by needle or lancet. An individual then coats a paper strip carrying chemistry with the blood, and finally insert the blood-coated strip into a blood glucose meter for measurement of glucose concentration by determination of change in reflectance.

There are numerous devices currently available for diabetics to monitor the level of blood glucose. The best of these devices require the diabetic to prick a finger and to collect a drop of blood for placement on a strip, which is inserted into a monitor that determines the level of glucose in the blood. Pricking one's finger tends to be painful. Moreover, a relatively large wound is produced by the pricking device, typically a lancet or a needle. It is known that the pain arising from the finger prick deters diabetics from compliance with the monitoring regimen. Lack of compliance increases the risk of complications due to diabetes. Thus there is a need for a more painless and less traumatic means of collecting biological samples for monitoring one's level of glucose in blood.

Several patents have proposed that the level of glucose in blood can be monitored by measuring the level of glucose in interstitial fluid. In order to obtain samples of interstitial fluid, the barrier function of the stratum corneum must be overcome. Jacques, U.S. Pat. No. 4,775,361, discloses a method of ablating the stratum corneum of a region of the skin of a patient by using pulsed laser light of a wavelength, pulse length, pulse energy, pulse number, and pulse repetition rate sufficient to ablate the stratum corneum without significantly damaging the underlying epidermis. This patent discloses the use of laser light having a wavelength of 193 nm or 2940 nm. Laser light having wavelengths of 193 nm or 2940 nm can be provided by an excimer or Er:YAG light source, respectively, both of which are extremely expensive.

Tankovich, U.S. Pat. No. 5,423,803, discloses a process for the removal of superficial epidermal skin cells in the human skin. A contaminant having a high absorption in at least one wavelength of light is topically applied to the surface of the skin. Some of the contaminant is forced to infiltrate into spaces between superficial epidermal cells. The skin section is illuminated with short laser pulses at the above wave-length, with at least at least one of the pulses having sufficient energy to cause some of the particles to explode tearing off the superficial epidermal cells. In a preferred embodiment, the contaminant includes 1 micron graphite particles and the laser used in a Nd:YAG laser.

Zahrov, WO 94/09713, discloses a method for perforating skin comprising the steps of (a) focusing a laser beam in the shape of an ellipse at the surface of the skin with sufficient energy density to create a hole at least as deep as the keratin layer and at most as deep as the capillary layer; and (b) creating at least one hole, each hole having a width between 0.05 and 0.5 mm and a length of equal to or less than 2.5 mm. This patent discloses a variety of lasers suitable for carrying out this method. However, the method disclosed in Zahrov is limited to light source having a wavelength of 2940 nm. As stated previously, laser light of this wavelength can be provided by a Er:YAG light source, which is very expensive. Moreover, such a light source is relatively large, with the result that it would not be practical for use in a hand-held device.

In all of the methods involving forming an opening in the skin by means of a laser, a focused laser beam is used to form a small opening in the stratum corneum. A critical limitation of lasers in general is cost and power. The higher the power of a laser, the higher is its cost. If, in a desire to lower costs, a low power laser is used, the formation of an opening in the stratum corneum is preferably carried out by means of multiple light pulses. When multiple light pulses are used, it is desirable to cause each pulse, i.e., the first pulse and subsequent pulses, to strike the same area of the skin of the patient at the best focus, thereby increasing the efficiency of the application of light to the target, and minimizing the spreading of the light over a large area of the skin of the patient. However, because of random movement of the patient, it is difficult to maintain the focus of the laser at the best focus. Moreover, it is difficult to align the area to be struck by a given pulse with the area struck by a previously applied pulse.

It would be desirable to provide a method for providing an opening in the surface of the skin wherein an inexpensive light source is utilized, but wherein sufficient power is delivered within a short period of time. Thus, there is a need to focus, align, or both focus and align the laser between pulses to allow rapid and efficient opening of a region of the stratum corneum.

SUMMARY OF THE INVENTION

This invention provides methods and apparatus for focusing, aligning, or both focusing and aligning pulsed light on the surface of the skin of a patient. When the light is focused and aligned, the light can be used to form an opening, or pore, in the skin of the patient, from which opening or pore biological fluid can be obtained.

In one aspect, the invention involves a method for focusing light on a surface of skin of a patient. In general, the method for focusing light comprises the steps of:
(1) projecting at least one pulse of light, preferably driven at a level of energy that is insufficient to form an opening in the skin of the patient, onto the surface of the skin of the patient;
(2) collecting at least a portion of the light that is reflected from the skin of the patient;
(3) projecting the collected, reflected light onto a detector to provide a signal; and
(4) adjusting the projection of the pulsed light onto the surface of the skin of the patient in such a manner that the signal projected onto the detector is optimized.

When the pulsed light is properly focused, i.e., when it is characterized by the best focus, it can be used to provide energy to form an opening in the skin of the patient.

A preferred embodiment of a method for focusing light comprises the steps of:

(1) causing a pulsed beam of light, preferably driven at a level of energy that is insufficient to form an opening in the skin of the patient, to pass through a lens to project a spot on the surface of the skin of the patient;

(2) causing light that is reflected from the surface of the skin of the patient to pass through a lens to project a spot on a target on a detector; and (3) moving the lens that projected the spot on the surface of the skin of the patient in such a direction that the quantity of the light reflected from the surface of the skin of the patient and projected on the target on the detector indicates the best focus.

After the lens is moved, a pulsed beam of light, driven at a level of energy at which an opening in the skin can be formed, can be caused to pass through the lens to project a spot on the surface of the skin of the patient, whereby formation of an opening in the skin occurs.

In another preferred embodiment, the invention involves a method for focusing light comprising the steps of:

(1) providing a pulsed beam of collimated light, preferably driven at a level of energy that is insufficient to form an opening in the skin of the patient;

(2) allowing a majority of the light from the beam to be reflected off the surface of a semi-silvered mirror to be transmitted through a lens to a region of the surface of the skin of the patient, from which region a portion of the light of the transmitted beam is reflected, passes through the semi-silvered mirror, then passes through a lens to project a spot on a detector having a central detection zone and a peripheral detection zone surrounding the central detection zone; and (3) adjusting the lens that projected the spot on the surface of the skin of the patient so that the quantity of the light striking the central detection zone and the quantity of light striking the peripheral detection zone indicates the best focus.

After the lens is adjusted, a pulsed beam of light, driven at a level at which formation of an opening in the skin can occur, can be caused to pass through the lens to project a spot on the surface of the skin of the patient, whereby formation of an opening in the skin occurs.

As an alternative to the use of a semi-silvered mirror, a dichroic filter can be used to direct light to the skin from the light source and from the skin to the detector.

In another aspect, the invention involves a method for focusing and aligning light on a surface of skin of a patient. When more than one pulse of light is required to form an opening in the skin of the patient, aligning the light prior to each pulse will improve the efficiency of formation of the opening. In general, the method for aligning and focusing is the same as the method for focusing, with the difference being that aligning further includes a step for moving the spot of light formed by the source of light so that light strikes the surface of the skin at or near the position on the surface of the skin of the patient at which the previous spot of light struck the skin. In general, the method for focusing and aligning light comprises the steps of:

(1) projecting at least one pulse of light, preferably driven at a level of energy that is insufficient to form an opening in the skin of the patient, onto the surface of the skin of the patient;

(2) collecting at least a portion of the light that is reflected from the skin of the patient;

(3) projecting the collected, reflected light onto a detector to provide a signal; and (4) adjusting the projection of the pulsed light onto the surface of the skin of the patient in such a manner that the signal projected onto the detector is optimized.

When the pulsed light is properly focused and aligned, e.g., when it is characterized by the best focus and best alignment, it can be used to provide energy to form an opening in the skin of the patient.

A preferred embodiment of the method for focusing and aligning light comprises the steps of:

(1) causing a pulsed beam of light, preferably driven at a level of energy that is insufficient to form an opening in the skin of the patient, to pass through a lens to project a spot on the surface of the skin of the patient;

(2) causing light that is reflected from the surface of the skin of the patient to pass through a lens to project a spot on a target on a detector;

(3) moving the lens that projected the spot on the surface of the skin of the patient in such a direction that the quantity of the light reflected from the surface of the skin of the patient and projected on the target on the detector indicates the best alignment;

(4) moving the lens that projected the spot on the surface of the skin of the patient axially in such a direction that the quantity of the light reflected from the surface of the skin of the patient and projected on the target on the detector indicates the best focus.

After the lens is adjusted, a pulsed beam of light driven at a level at which formation of an opening in the skin can occur is caused to pass through the lens to project a spot on the surface of the skin of the patient, whereby formation of an opening in the skin occurs. Then steps (1), (2), (3), (4) and the opening-forming step can be repeated until the opening formed in the skin is of the desired size.

In another preferred embodiment, the invention involves a method for focusing and aligning light comprising the steps of:

(1) providing a pulsed beam of light, preferably driven at a level of energy insufficient to form an opening in the skin of the patient, to pass through a lens to project a spot on the surface of the skin of a patient;

(2) allowing a majority of the beam to pass through a semi-silvered mirror to be transmitted through a lens to a region of the surface of the skin of a patient, from which region a portion of the light of the transmitted beam is reflected, passes through the semi-silvered mirror, then passes through a lens to project a spot on a detector having a central detection zone and a peripheral detection zone surrounding the central detection zone, the peripheral detection zone preferably divided into segments; and (3) adjusting the lens that projected the spot on the surface of the skin of the patient so that the quantity of the light striking the central detection zone and the quantity of light striking the peripheral detection zone indicates the best alignment; and (4) adjusting the lens that projected the spot on the surface of the skin of the patient so that the quantity of the light striking the central detection zone and the quantity of light striking the peripheral detection zone indicates the best focus.

After the lens is adjusted, a pulsed beam of light driven at a level at which formation of an opening in the skin can occur is caused to pass through the lens to project a spot on the surface of the skin of the patient, whereby formation of an opening in the skin occurs. Then steps (1), (2), (3), (4) and the opening-forming step can be repeated until the opening formed in the skin is of the desired size.

As an alternative to the use of a semi-silvered mirror, a dichroic filter can be used to direct light to the skin from the light source and from the skin to the detector.

In another aspect, this invention involves a method for aligning light on the surface of the skin of a patient, which method comprises the steps of:

(1) projecting at least one pulse of light onto the surface of the skin of the patient;

(2) collecting at least a portion of the light that is reflected from the skin of the patient;

(3) projecting the collected, reflected light onto a detector to provide a signal;

(4) adjusting the projection of the pulsed light onto the surface of the skin of the patient in such a manner that the signal projected onto the detector is optimized.

When the pulsed light is properly aligned, e.g., when it is characterized by the best alignment, it can be used to provide energy to form an opening in the skin of the patient.

In a preferred embodiment, the invention involves a method for aligning light on the surface of the skin of a patient comprising the steps of:

(1) causing a pulsed beam of light to pass through a lens to project a spot on the surface of the skin of a patient;

(2) causing light that is reflected from the surface of the skin to pass through a lens to project a spot on a target on a detector; and (3) moving the lens that projected the spot on the surface of the skin of the patient in such a direction that the quantity of the light reflected from the surface of the skin of the patient and projected on the target on the detector indicates the best alignment.

In a preferred embodiment, the invention involves a method for forming an opening in the surface of the skin of a patient comprising the steps of:

(1) causing a pulsed beam of light, driven at a level of energy that is insufficient to form an opening in the skin of the patient, to pass through a lens to project a spot on the surface of the skin of the patient;

(2) causing light that is reflected from the surface of the skin to pass through a lens to project a spot on a target on a detector;

(3) moving the lens that projected a spot on the surface of the skin of a patient in such a direction that the quantity of the light reflected from the surface of the skin of the patient and projected on the target on the surface of the detector indicates the best alignment; and (4) causing a beam of light, driven at a level of energy at which an opening in the skin can be formed, to pass through a lens to project a spot on the surface of the skin of the patient, whereby formation of an opening in the skin occurs.

After the lens is adjusted, a pulsed beam of light driven at a level at which formation of an opening in the skin can occur is caused to pass through the lens to project a spot on the surface of the skin of the patient, whereby formation of an opening in the skin occurs. Then steps (1), (2), (3), (4) and the opening-forming step can be repeated until the opening formed in the skin is of the desired size.

The use of the method of this invention eliminates the need for two sources of light, namely a first source of light for focusing or aligning or focusing and aligning the light that forms the opening and a second source of light for forming an opening in the skin. The same source of light used for focusing or aligning the opening-forming light can be used for forming an opening in the skin. By using the same source of light for focusing and aligning and for forming an opening in the skin, the errors that typically arise when using a focusing light separate from the opening-forming light are reduced.

In another aspect, the invention involves an apparatus suitable for focusing and aligning light. In general, the apparatus-comprises (a) a source of pulsed light, (b) a means for projecting pulsed light onto the surface of the skin of a patient, (c) a means for adjusting for alignment and focus of the pulsed light, and (d) a means for collecting light reflected from the surface of the skin and projecting the collected, reflected light onto a detector to determine the adjustment required for best alignment and best focus.

In a preferred embodiment, the apparatus comprises:

(a) a source of pulsed light, capable of being driven at a level of energy at which formation of an opening in the skin cannot occur;

(b) a lens for collimating light from said source of pulsed light;

(c) a mirror for reflecting a majority of the collimated light or a dichroic filter for transmitting a majority of the collimated light;

(d) a lens for focusing light reflected from the mirror or transmitted from the filter onto a region of the surface of the skin of a patient;

(e) a lens for focusing light reflected from the region of the skin onto a detector.

The detector is preferably the type of detector that has a central detection zone surrounded by a peripheral detection zone.

The foregoing apparatus may further include a mechanism for moving the focusing/alignment lens when the detector indicates that movement would reduce the distance between the spots on the skin struck by successive pulses of light. Alternatively, other means for adjusting the focusing and alignment or both include, but are not limited to, mechanisms for moving the entire apparatus, mechanisms for moving the source of light, mechanisms for moving the lenses, and the like.

The invention makes it possible to minimize the number of pulses of light needed to form an opening in the surface of the skin of a patient. Alternatively, the invention makes it possible to cause a given pulse of light to strike the skin at a position different from that struck by a previous pulse of light.

DETAILED DESCRIPTION

Figure 1:
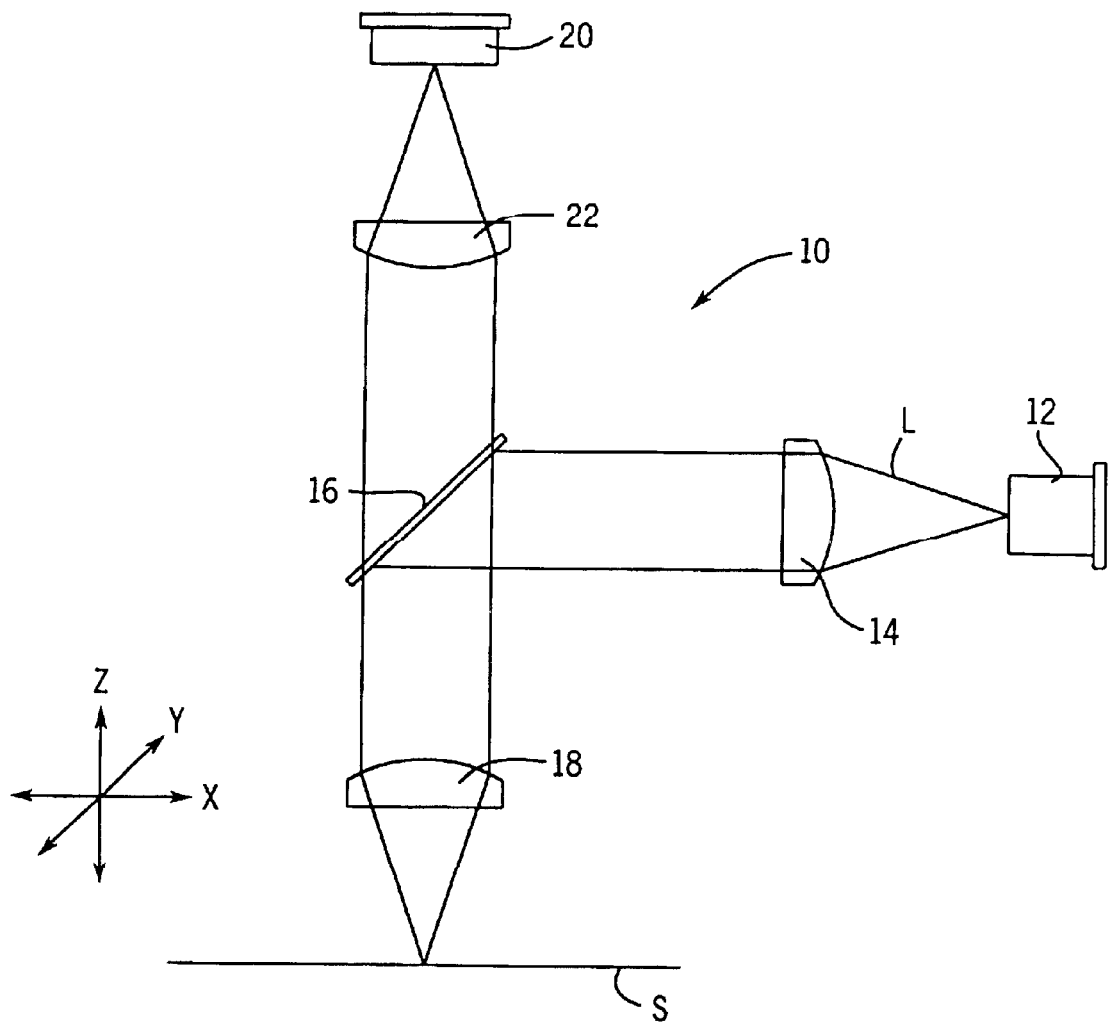
FIG. 1 is a schematic view of an apparatus suitable for use in this invention.

As used herein, the expression "surface of the skin", and the like, is intended to include the surface of the skin in an untreated condition and the surface of the skin in a treated condition. The surface of the skin in the untreated condition simply means the bare surface of the skin. The surface of the skin in the treated condition means the bare surface of the skin onto which is applied a material capable of absorbing light at some wavelength. The particular type of application of the material is not critical and includes, but is not limited to, a coating of light absorbing material applied as a liquid, gel, powder, and the like, a layer of light absorbing material applied as a tape, a strip, a layer, a sheet, and the like.

As used herein, the expression "best focus" means the distance of the lens from the surface of the skin that provides a spot on the skin of a size that generates the desired opening in the skin. As used herein, the expression "best alignment" means the distance between a pre-determined location on the surface of the skin of a patient and the location at which the pulsed light strikes the surface of the skin is as close to zero as can be effected with a given apparatus. As used herein, the term "pre-determined" means determined prior to the emission of a given pulse of light. Typically, suitable pre-determined ranges are determined by trial-and-error. As used herein, the term "spot" is intended to include, but is not limited to, a spot of any shape, such as, for example, circular, elliptical, and so forth. As used herein, the term "optimized" means that the light is projected, as by reflection, onto the detector such that the distribution of the light is characterized by the best focus. As used herein, the expression "a level of energy at which formation of an opening in the skin can occur" includes (a) a level of energy at which the desired opening in the skin can be caused to occur with a single pulse of light and (b) a level of energy at which a partial opening in the skin can be caused to occur with a single pulse of light but at which the desired opening can be caused to occur only with multiple pulses of light.

This invention involves methods for focusing, aligning, or both focusing and aligning pulsed light so that the light strikes the desired position on a region of the skin of a patient. The desired position includes both desired depth position, which involves focusing, and desired regional position, which involves alignment. These methods can be followed by a method for forming an opening in the surface of the skin by means of pulsed light. From the thus-formed opening, biological fluid, e.g., blood or interstitial fluid, can be collected for use in an assay to determine the presence and/or concentration of an analyte, e.g. glucose, in the biological fluid.

Proper focusing of light is necessary to form an opening in the skin of a given size with a low expenditure of power within a short period of time. If the light is not properly focused, a greater period of time and a greater amount of power are required than if the light is properly focused. Moreover, if the light is not properly focused, the size of the opening in the skin may be too large or too small. If the opening is too large, healing of the wound may require an excessive amount of time. If the opening is too small, the difficulty of obtaining biological fluid within a reasonable period of time is increased.

Proper alignment of light is necessary for the same reasons as is proper focusing of light. If the light is not properly aligned, a greater period of time and a greater amount of power are required than if the light is properly aligned. One benefit of proper alignment is to cause each pulse of light that is optimally focused to strike substantially the same position on a region of the skin, thereby minimizing the number of pulses of light needed to form an opening or pore in the skin at that position. Alternatively, another benefit of proper alignment is to cause each pulse of light that is optimally focused to strike a different position of the skin from that struck by a previous pulse, so that a plurality of openings can be formed in the skin in a given region of the skin.

In summary, improper focusing can lead to thermal damage to tissue surrounding the opening in the skin and inefficient formation of openings in the skin. Improper alignment can lead to increasing the area of tissue damage on the skin.

In general, the method for focusing and aligning light comprises the steps of:
  (1) projecting at least one pulse of light, preferably driven at a level of energy insufficient to form an opening in the skin of the patient, onto the surface of the skin of the patient;
  (2) collecting at least a portion of the light that is reflected from the surface of the skin of the patient;
  (3) projecting the collected, reflected light onto a detector to provide a signal; and
  (4) adjusting the projection of the pulsed light on the surface of the skin in such a manner that the signal projected onto the detector is optimized.

A preferred method for focusing and aligning pulsed light comprises the following steps:
  (1) causing a pulsed beam of collimated light, preferably driven at a level of energy insufficient to form an opening in the skin of the patient, to pass through a lens to project a spot on the surface of the skin of a patient;
  (2) causing light that is reflected from the surface of the skin of the patient to pass through a lens to project a spot on a target on a detector;
  (3) moving the lens that projected the spot on the surface of the skin of the patient in such a direction that the quantity of the light reflected from the surface of the skin of the patient and projected on the target on the detector indicates the best alignment; and
  (4) moving the lens that projected the spot on the surface of the skin of the patient in such a direction that the quantity of the light reflected from the surface of the skin of the patient and projected on the target on the detector indicates the best focus.

In a preferred embodiment utilizing reflection of collimated light from a mirror, the method for focusing and aligning comprises the steps of:
  (1) providing a pulsed beam of collimated light, preferably driven at a level of energy insufficient to form an opening in the skin of the patient;

(2) allowing a majority of the beam to reflect off the surface of a semi-silvered mirror to be transmitted through a lens to a region of the surface of the skin, from which region a portion of the light of the transmitted beam is reflected, passes through the semi-silvered mirror, then passes through a lens to focus on a bulls-eye detector having a central detection zone and a peripheral detection zone surrounding the central detection zone; and (3) moving the lens that projected the spot on the surface of the skin of the patient in such a direction that the quantity of the light reflected from the surface of the skin of the patient and projected on the target on the detector indicates the best alignment; and (4) adjusting the lens that projected the spot on the surface of the skin of the patient so that the quantity of the light striking the central detection zone and the quantity of light striking the peripheral detection zone indicates the best focus.

FIG. 1 is a schematic diagram of an embodiment of an apparatus suitable for carrying out this invention. The apparatus 10 comprises a source of light 12, which transmits a beam of light, designated by the letter "L". The source of light is preferably a laser. Other sources of light include, but are not limited to, light emitting diodes, flash lamps, and the like. During both the aligning phase and the focusing phase, the level of power is sufficiently low so that no opening will be formed in the surface of the skin. The beam of light is collimated by a lens 14. The beam of collimated light strikes a semi-silvered mirror 16. A majority of the light is reflected; a minority of the light is transmitted. The reflected light is focused on the surface of the skin, designated by the letter "S" by a lens 18. A portion of the light striking the skin is reflected back through the lens 18 and through the mirror 16. The light passing through the mirror 16 is then focused onto a bulls-eye detector 20 by means of a lens 22.

When the light reflected from the surface of the semi-silvered mirror is properly aligned on the skin, it is also properly aligned on the central detection zone 24 of the bulls-eye detector 20. When the light reflected from the surface of the semi-silvered mirror is not properly aligned on the skin, a greater quantity of light strikes the peripheral detection zone 26 of the bulls-eye detector 20 than would be the case when the light is properly aligned. The lens 18 is moved as necessary (i.e., substantially parallel to the surface of the skin) to cause the optimal amount of the transmitted light to strike the central detection zone 24 of the bulls-eye detector 20. When the light is properly aligned, the light can then be used to provide a pulsed beam of light having a level of energy sufficiently high to form an opening in the skin.

When the light reflected from the surface of the semi-silvered mirror is properly focused on the skin, it is also properly focused on the central detection zone 24 of the bulls-eye detector 20. See FIG. 2A. When the light reflected from the surface of the semi-silvered mirror is not properly focused on the skin, a greater quantity of light strikes the peripheral detection zone 26 of the bulls-eye detector 20 than would be the case when the light is properly focused. See FIG. 2B. The lens 18 is moved as necessary (i.e., substantially perpendicular to the surface of the skin) to cause the optimal amount of the transmitted light to strike the central detection zone 24 of the bulls-eye detector 20. When the light is properly focused, the light can then be used to provide a pulsed beam of light having a level of energy sufficiently high to form an opening in the skin Sources of light that are suitable for use with this invention include, but are not limited to, lasers. Lasers suitable for forming an opening in the skin to draw biological fluid are well-known to those of ordinary skill in the art. See for example, U.S. Pat. Nos. 4,775,361, 5,165,418, 5,374,556, International Publication Number WO 94/09713, Lane et al. (1984) IBM Research Report—"Ultraviolet-Laser Ablation of Skin", and WO 97/07734, all of which are incorporated herein by reference. Lasers that are suitable for forming an opening in the skin the skin include, but are not limited to, Er:YAG, Nd:YAG, He:Ne, and semiconductor lasers. Lasers suitable for use in this invention include, but are not limited to, diode lasers, gas lasers, and pumped lasers. It is preferred that the laser be capable of providing pulsed light. It is further preferred that the laser be capable of modulating the intensity of the light. Flash lamps, e.g., sources of pulsed high intensity white light, are also suitable for use with this invention. Light emitting diodes are also suitable for use in this invention.

Collimating lenses suitable for use in this invention are well-known to those of ordinary skill in the art.

Mirrors suitable for this invention include, but are not limited to, silver, gold, aluminum, and copper. It is preferred that the mirror be capable of reflecting at least 90% of the light that strikes it. Although mirrors are preferred, suitable alternatives for the mirror include such devices as dichroic filters, which may alternatively be referred to as dichromatic filters.

Lenses suitable for use in this invention are well-known to those of ordinary skill in the art. The lenses can be maneuvered into proper position by electromechanical actuators, such as motors, solenoids, and voice coils.

Detectors suitable for use in this invention should be capable of measuring the intensity of the light at a specific wavelength of the light source. Representative examples of detectors suitable for use in this invention include bulls-eye detectors, array detectors, and quadrant detectors. Detectors are well-known to those of ordinary skill in the art and are commercially available.

Figure 2A:
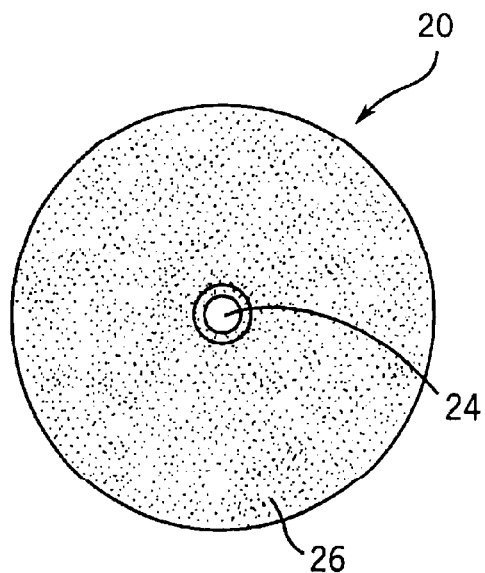
FIG. 2A is a top view of a spot of light striking a bulls-eye detector wherein the spot is in focus and the light is properly aligned.
Figure 2B:
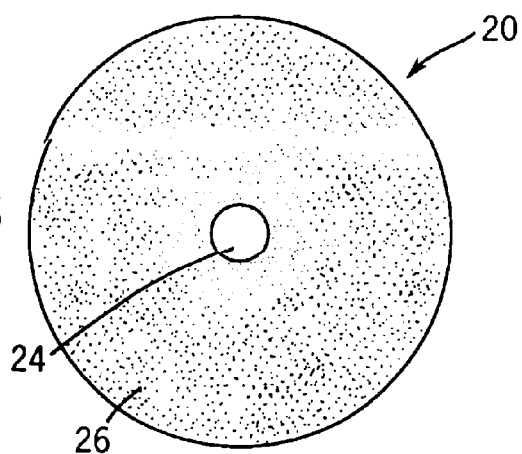
FIG. 2B is a top view of a spot of light striking the detector wherein the spot is out of focus.
Figure 3:
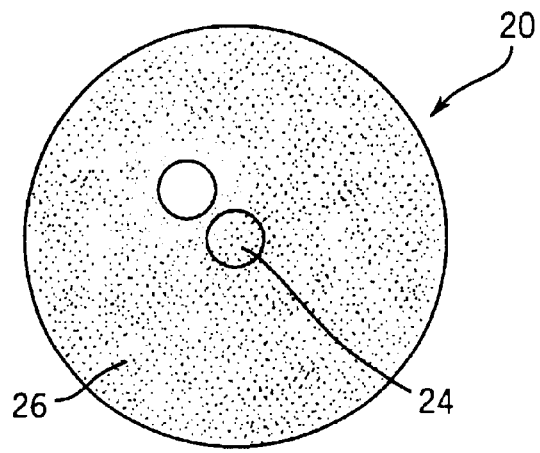
FIG. 3 is a top view of a spot of light striking a bulls-eye detector wherein the light is out of alignment.

There are at least two types of bulls-eye detectors. In the simplified bulls-eye detector, as shown in FIGS. 2A, 2B, and 3, the detector 20 comprises a central detection zone 24 surrounded by at least one peripheral detection zone 26. The central detection zone can be in the shape of a circle. The peripheral detection zone or zones, which surround the central detection zone, can be in the shape of an annular ring or concentric annular rings. When this type of detector is used, alignment is carried out by moving the focusing lens in a direction parallel to the surface of the skin in order to maximize the signal on the central detection zone 24. FIG. 3 illustrates the manner in which light is projected on the detector when the light projected onto the skin is both misaligned and out of focus. When using this type of detector, alignment is carried out by a search method such as a left to right, top to bottom scanning motion. Once the spot is aligned, the focusing lens is moved in a direction perpendicular to the surface of the skin to obtain the best focus. In general, it is preferred to align the light before it is focused. The defocused beam spreads the light over a greater area of the detector. Only when both regions of the detector, i.e., the central detection zone and the peripheral detection zone, are measuring light can the magnitude of the misalignment be measured. It should be noted that with the simplified bulls-eye detector, only the magnitude, not the direction, of the misalignment can be measured. FIG. 2B illustrates the manner in which light is projected onto the bulls-eye detector when the light is not optimally focused. FIG. 2A illustrates the manner in which light is projected onto the bulls-eye detector when the light is optimally focused.

Figure 5A:
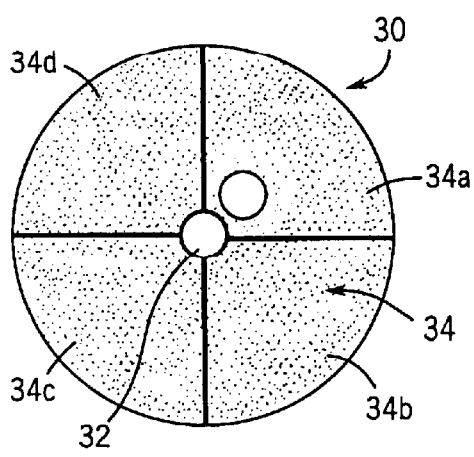
FIG. 5A is a schematic view of a bulls-eye detector wherein the peripheral zone is divided into quadrants and the spot of light is not aligned.
Figure 5B:
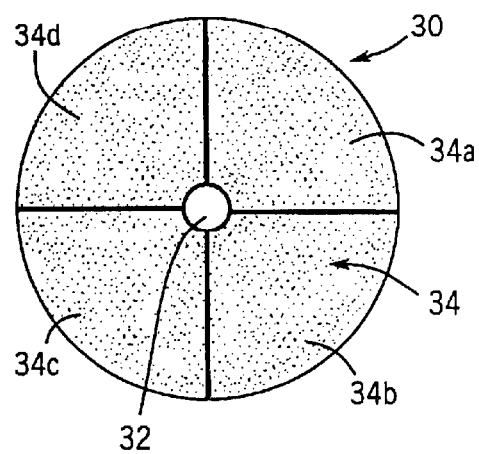
FIG. 5B is a schematic view of a bulls-eye detector wherein the peripheral zone is divided into quadrants and the spot of light is properly aligned and properly focused.

In the modified bulls-eye detector, the modification involves dividing the annular region of the detector into a plurality of segments. In FIGS. 5A and 5B, the detector 30 has a central detection zone 32 and a peripheral detection zone 34, which is divided into four segments 34a, 34b, 34c, and 34d, or quadrants. The detector can have more than four segments or less than four segments. Because four separate detectors surround the central detection zone, a direct determination of both magnitude and direction of the misalignment can be made. Thus, a direct one step alignment can be made. As with the simplified bulls-eye detector, this process is improved when the incident light is spread over multiple detector segments, as when the system is defocused.

Figure 4A:
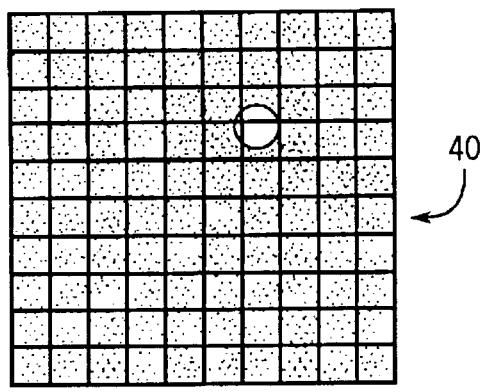
FIG. 4A is a top view of a spot of light striking an array detector wherein the spot of light is not aligned and not properly focused.
Figure 4B:
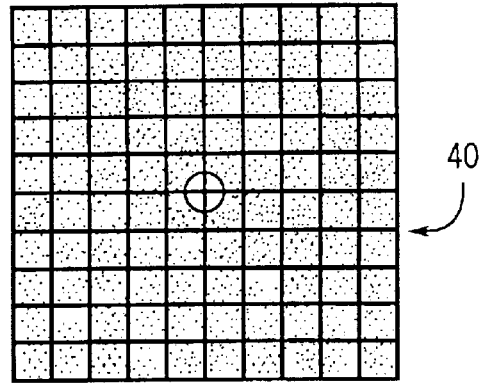
FIG. 4B is a top view of a spot of light striking an array detector wherein the spot of light is properly aligned and properly focused.

Another type of detector suitable for use in the invention, which is illustrated in FIGS. 4A and 4B, is an area array detector 40. Although the area array detector requires greater complexity in electronics to process the larger number of detection elements, direct determination of both alignment and focus are easily made. High resolution area array detectors such as the CCD or photodiode arrays used in video cameras or image capture systems allow an additional capability over the bulls-eye type detectors. Because of their ability to image the skin, the high resolution area array detectors can provide information about non-functional regions on the skin, such as regions covered by a hair of the body.

Figure 6:
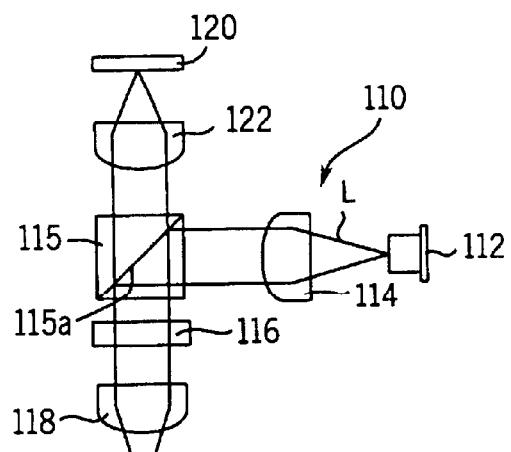
FIG. 6 is a schematic view of an apparatus suitable for use in this invention, wherein a polarizing beam splitter is used to direct the light toward the skin.
Figure 7:
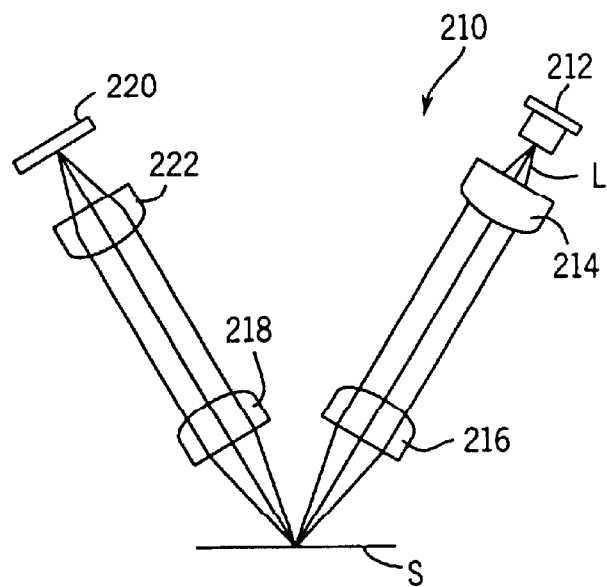
FIG. 7 is a schematic view of an apparatus suitable for use in this invention, wherein the incident beam and the beam reflected from the skin are separated by an angle.
Figure 8:
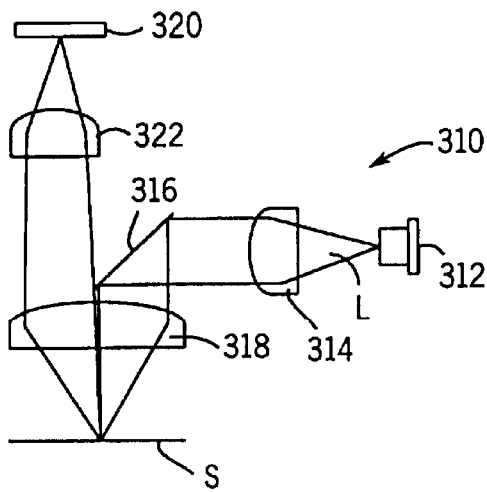
FIG. 8 is a schematic view of an apparatus suitable for use in this invention, wherein same the illuminating beam and the detected beam share the same aperture.

FIGS. 6, 7, and 8 show three alternate optical architectures that are functionally equivalent to the optical arrangement described previously. FIG. 6 shows a schematic drawing of an apparatus that uses a polarizing beam splitter to direct the light toward the skin. The apparatus 110 comprises a source of light 112, which transmits a beam of light, designated by the letter "L". During both the aligning phase and the focusing phase, the level of power is sufficiently low so that no opening will be formed in the surface of the skin. The beam of light is collimated by a lens 114. The beam of collimated light encounters a polarizing beam splitter 115. The horizontally polarized beam is reflected by the hypotenuse face 115a of the polarizing beam splitter 115. The reflected beam then passes through a quarter wave linear retarder 116 oriented at a 45° angle (with respect to the horizontal plane defined by the polarization state), thereby converting the beam to right circularly polarized light. The right circularly polarized light then passes through a lens 118 to strike the surface of the skin, designated by the letter "S". The specular reflection from the surface of the skin converts the polarization state to left circularly polarized light (due to the coordinate transformation from reflection). The left circularly polarized light is converted to vertically polarized light as it passes through the quarter wave retarder 116 in the opposite direction. The vertically polarized light is then transmitted through the polarizing beam splitter 115 onto the detector 120 by means of a lens 122. If the source of light is a semi-conductor laser, it is oriented such that the beam of light is horizontally polarized (polarized within the plane of the page). If the source of light provides unpolarized light, a linear polarizer (shown/not shown) is placed in the beam with its transmission axis oriented horizontally.

When the light reflected from the polarizing beam splitter 115 is properly aligned on the skin, it is also properly aligned on the central detection zone 124 of the bulls-eye detector 120. When the light reflected from the polarizing beam splitter 115 is not properly aligned on the skin, a greater quantity of light strikes the peripheral detection zone 126 of the bulls-eye detector 120 than would be the case when the light is properly aligned. The lens 118 is moved as necessary (i.e., substantially parallel to the surface of the skin) to cause the optimal amount of the transmitted light to strike the central detection zone 124 of the bulls-eye detector 120. When the light is properly aligned, the light can then be used to provide a pulsed beam of light having a level of energy sufficiently high to form an opening in the skin.

When the light reflected from the polarizing beam splitter 115 is properly focused on the skin, it is also properly focused on the central detection zone 124 of the bulls-eye detector 120. When the light reflected from the polarizing beam splitter 115 is not properly focused on the skin, a greater quantity of light strikes the peripheral detection zone 126 of the bulls-eye detector 120 than would be the case when the light is properly focused. The lens 118 is moved as necessary (i.e., substantially perpendicular to the surface of the skin) to cause the optimal amount of the transmitted light to strike the central detection zone 124 of the bulls-eye detector 120. When the light is properly focused, the light can then be used to provide a pulsed beam of light having a level of energy sufficiently high to form an opening in the skin.

FIG. 7 shows a schematic drawing of an apparatus in which the incident beam of light and beam of light reflected from the skin are separated by an angle. The apparatus 210 comprises a source of light 212, which transmits a beam of light, designated by the letter "L". During both the aligning phase and the focusing phase, the level of power is sufficiently low so that no opening will be formed in the surface of the skin. The beam of light is collimated by a lens 214. The beam of collimated light passes through lens 216 and strikes the surface of the skin, designated by the letter "S". The skin is illuminated at an angle of 30° (from the skin surface normal). The specular reflection from the skin is collected also at a 30° angle. Although 30° angles are shown, other angles may be chosen. The choice of angles is dictated by the desired geometry of the opening to be formed in the skin, the size of the components needed to secure the lenses, and other considerations involving mechanical devices. A portion of the light striking the skin is reflected back through a lens 218. The light is then focused onto a bulls-eye detector 220 by means of a lens 222.

When the light reflected from the surface of the skin is properly aligned on the skin, it is also properly aligned on the central detection zone 224 of the bulls-eye detector 220. When the light reflected from the surface of skin is not properly aligned on the skin, a greater quantity of light strikes the peripheral detection zone 226 of the bulls-eye detector 220 than would be the case when the light is properly aligned. The lens 218 is moved as necessary (i.e., substantially parallel to the surface of the skin) to cause the optimal amount of the transmitted light to strike the central detection zone 224 of the bulls-eye detector 220. When the light is properly aligned, the light can then be used to provide a pulsed beam of light having a level of energy sufficiently high to form an opening in the skin.

When the light reflected from the surface of the skin is properly focused on the skin, it is also properly focused on the central detection zone 224 of the bulls-eye detector 220. When the light reflected from the surface of the skin is not properly focused on the skin, a greater quantity of light strikes the peripheral detection zone 226 of the bulls-eye detector 220 than would be the case when the laser light is properly focused. The lens 218 is moved as necessary (i.e., substantially perpendicular to the surface of the skin) to cause the optimal amount of the transmitted light to strike the central detection zone 224 of the bulls-eye detector 220. When the light is properly focused, the light can then be used to provide a pulsed beam of light having a level of energy sufficiently high to form an opening in the skin.

FIG. 8 shows a schematic drawing of an apparatus in which the illumination beam and detection beam share the same aperture. The apparatus 310 comprises a source of light 312, which transmits a beam of light, designated by the letter "L". During both the aligning phase and the focusing phase, the level of power is sufficiently low so that no opening will be formed in the surface of the skin. The beam of light is collimated by a lens 314. The beam of collimated light strikes a mirror 316. The light reflected from the mirror 316 is focused on the surface of the skin, designated by the letter "S" by a lens 318. The mirror illuminates half of the aperture of lens 318. A portion of the light striking the skin is reflected back through the lens 318. All of the light reflected from the skin passes through the lens 318. Half the light reflected from the skin and passing through the lens 318 is directed toward the source of light, and the other half is directed toward the detector. The light passing through the lens 318 is then focused onto a bulls-eye detector 320 by means of a lens 322.

When the light reflected from the surface of the mirror 316 is properly aligned on the skin, it is also properly aligned on the central detection zone 324 of the bulls-eye detector 320. When the light reflected from the surface of the mirror 316 is not properly aligned on the skin, a greater quantity of light strikes the peripheral detection zone 326 of the bulls-eye detector 320 than would be the case when the light is properly aligned. The lens 318 is moved as necessary (i.e., substantially parallel to the surface of the skin) to cause the optimal amount of the transmitted light to strike the central detection zone 324 of the bulls-eye detector 320. When the light is properly aligned, the light can then be used to provide a pulsed beam of light having a level of energy sufficiently high to form an opening in the skin.

When the light reflected from the surface of the mirror 316 is properly focused on the skin, it is also properly focused on the central detection zone 324 of the bulls-eye detector 320. When the light reflected from the surface of the mirror 316 is not properly focused on the skin, a greater quantity of light strikes the peripheral detection zone 326 of the bulls-eye detector 320 than would be the case when the light is properly focused. The lens 318 is moved as necessary (i.e., substantially perpendicular to the surface of the skin) to cause the optimal amount of the transmitted light to strike the central detection zone 324 of the bulls-eye detector 320. When the light is properly focused, the light can then be used to provide a pulsed beam of light having a level of energy sufficiently high to form an opening in the skin.

OPERATION

In the preferred embodiments, a photosensitive dye is used to cover the region of the skin that is to be struck by the pulsed laser light. Photosensitive dyes that are suitable for use in this invention should be coordinated with the laser selected for use in the invention. For example, if the light from the laser has a given wavelength, such as 880 nm, the photosensitive dye should be able to absorb light at that wavelength, i.e., 880 nm. Representative examples of classes of dyes include the polymethine, porphine, indathrene, quinone, and triphenylmethane classes of dyes.

As used herein, the expression "photosensitizing material" means a compound or mixture of compounds that absorb electromagnetic radiation. These compounds are commonly referred to as chromophores. In general, photosensitizing materials include, but are not limited to, photothermal materials, photochemical, and photomechanical materials. Photothermal materials are compound, or mixtures of compounds, that absorb electromagnetic radiation and radiate thermal energy. Photochemical materials are those in which a chemical reaction occurs as a result of absorbing electromagnetic energy. Photomechanical materials are those in which a physical response, e.g., explosion of particles, generation of a pressure wave, occurs as a result of absorbing electromagnetic energy. As used herein, the expression "photosensitizing assembly" means a structure comprising at least one layer containing a photosensitizing material. The structure may take the form of a film, sheet, block, membrane, gel, woven fabric, non-woven fabric, or combination of the foregoing. As used herein, the term "polymer" means a compound containing repeating structural units. The repeating structural units, i.e., monomers, include, but are not limited to, cellulosics, alkylene, ester, carbonate, amide, acrylic, agar, vinyl, and the like. As used herein, the term "adhesive" means a compound, or mixture of compounds, that promote adhesion between two surfaces.

A photosensitizing material can be provided in such a manner that it can be applied to skin in a reproducible manner, i.e., the quantity of photosensitizing material to which the skin is exposed can be known accurately.

Photosensitizing materials suitable for use in this invention are capable of absorbing electromagnetic radiation at one or more wavelengths. Electromagnetic radiation considered to be suitable for this invention include radiation from the ultraviolet, visible and infrared regions of the electromagnetic spectrum. It is preferred, however, that visible radiation and infrared radiation be employed. Ultraviolet radiation has a wavelength ranging from about 10 nm to about 380 nm. Visible radiation has a wavelength ranging from about 380 nm to about 780 nm. Infrared radiation has a wavelength ranging from about 780 nm to about 50,000 nm. Photosensitizing materials suitable for use in this invention include, but are not limited to, dyes and pigments. The term "pigment" is used to describe the class of colorants that are practically insoluble in the media in which they are applied. Pigments retain a particulate form, suspended in the media. The term "dye" is used to describe colorants that are soluble, or at least partially soluble, in the media in which they are applied. Dyes exhibit an affinity to the substrate to which they are applied. Classes of dyes that are suitable for use in this invention include, but are not limited to, diphenylmethane dyes, methine-polymethine dyes, porphine dyes, indathrene dyes, quinones, dithiol metal complexes, dioxazines, dithiazines, polymeric chromophores. Classes of pigments that are suitable for use in this invention include, but are not limited to, carbon black, carbon based pigments, metals, metal sols, dyed latexes, inorganic pigments. Colorants that are preferred for this invention include, but are not limited to, copper phthalocyanine, indocyanine green, nigrosin, prussian blue, colloidal silver (20 to 100 nm diameter), carbon black, IR-780, IR-140, irgalan black, naphthol green B, tellurapyryllium, and vanadyl tetra-t-butyl-naphthalocyanine. In either case, particles of the dyes or pigments must be of a size that they can readily be blended with carrier materials. Carrier materials suitable for use with dyes and pigments include, but are not limited to, solid polymers, adhesives, gels, inks. These materials comprise polymeric materials such as acrylics, silicones, polyesters, polycarbonates, polyimides, cellulosics, polyvinyl derivatives, polyethylene, polypropylene, and the like. It is preferred that the particles of dyes and pigments have a major dimension, e.g., length, diameter, no greater than about 50 µm.

The photosensitizing material should not adversely affect the patient. The photosensitizing material should be able to withstand elevated temperatures. The photosensitizing material preferably does not melt or decompose at temperatures below about 120° C. The photosensitizing material should be capable of absorbing a sufficient amount of light to convert it to an amount of thermal energy sufficient to cause permeation of the skin.

In one embodiment of this invention, the photosensitizing material can be applied to a substrate by means of a carrier. The carrier is a material in which the photosensitizing material can be uniformly dissolved if a dye or uniformly suspended if a pigment. Carriers that are suitable for uniformly suspending dyes include, but are not limited to, solid polymers, adhesives, gels, inks. Carriers that are suitable for uniformly suspending pigments include, but are not limited to, solid polymers, adhesives, gels, inks. The concentration of photosensitizing material in the carrier can vary. However, that concentration must be sufficient to provide the level of energy required for the desired function within the desired period of time. For example, if the desired function is to permeate the stratum corneum, and the selected photosensitizing material is carbon black, and the selected carrier is acrylic adhesive, and the selected source of energy is a laser diode (e.g., 810 nm), then the concentration of photosensitizing material in the carrier should be sufficient to absorb at least 10% of the input energy, preferably 50% of the input energy, more preferably 90% of the input energy. This parameter can also be expressed in terms of the rate of heat generation in watts per cubic centimeter. A sufficient concentration of dye is typically that required to obtain an optical density greater than 1.0 at the wavelength of the laser. Determination of the appropriate concentration can readily be determined by trial-and-error by one of ordinary skill in the art.

In addition to the photosensitizing material, other ingredients that can be added to the carrier in addition to the photosensitizing material include, but are not limited to, plasticizers, surfactants, binders, crosslinking agents. These materials are commercially available.

Substrates to which the carrier containing the photosensitizing material can be applied include, but are not limited to, polymeric materials, cloth, non-woven materials, microporous membranes, glass, and metal foils. The substrate is preferably sufficiently flexible to allow close contact with the skin. The substrate should adhere sufficiently to the carrier so that it does not detach before or during use, but only after removal from the skin. Both the substrate and the carrier should be biocompatible so that neither of them adversely affect the patient. Materials that are suitable for preparing the substrate include, but are not limited to, polyesters, polyimides, polyethylenes, polypropylenes, polycarbonates, acrylics, cellulose, derivatives of cellulose, and the like.

In embodiments wherein photosensitizing material is blended with a film-forming material, the film-forming material is preferably capable of being formed into a film that will allow uniform suspension of the photosensitizing material and will allow sufficient flexibilty to conform to the skin of the patient. Film-forming materials suitable for use in this embodiment include, but are not limited to, polyesters, polyimides, polyethylenes, polypropylenes, polycarbonates, acrylics, cellulose, derivatives of cellulose, and the like.

To prepare the photosensitizing assembly of the first embodiment, the photosensitizing material, e.g., a dye or pigment, is first mixed with the carrier to form a uniform suspension of photosensitizing material in the carrier. The thus-formed uniform suspension is then applied to a substrate, preferably by means of coating, printing, direct transfer. The thus-applied carrier is then cured, preferably by means of heat or radiation. In order to ensure enhanced adhesion between the mixture and the substrate, a layer of priming material can be interposed between the carrier and the substrate. Priming materials suitable for such a purpose are well-known to one of ordinary skill in the art and are commercially available.

To prepare the film of the second embodiment, the photosensitizing material, e.g., the dye or pigment, is mixed with the film-forming material to form a uniform suspension of photosensitizing material in the film-forming material. The resulting mixture is then formed into a film, preferably by means of extrusion, casting, or molding. These techniques are well-known to one of ordinary skill in the art.

The photosensitizing assembly or the photosensitizing film can be applied to the skin in a variety of ways. In the case of the photosensitizing assembly, the carrier can be a pressure-sensitive adhesive. The adhesive can adhere the assembly to the skin. In the case of the photosensitizing film, the film can be adhered to the skin by means of electrostatic force. Other means of attachment include pressure applied to the film and vacuum to draw the film or photosensitizing assembly into contact with the skin. Combinations of means of attachment can also be used.

In order to carry out this invention, the device 10 is placed in proximity to a region of the skin, which is coated with an appropriate dye. The source of light 12 is pulsed. The light from the source of light 12 is collimated by means of a lens 14. The collimated light is reflected from a semi-silvered mirror 16. The mirror 16 reflects a majority of the light, allowing only a minority of the light to pass. During the focusing phase of the operation, the source of light 12 is driven at a low level of power, the level being sufficiently low that no opening can be formed in the skin. A spot of light is projected on the surface of the skin, which, as stated previously, is coated with an appropriate dye. Some of the light projected to the spot on the skin is reflected off the skin. This reflected light passes back first through the lens 18 and then through the mirror 16. This light then passes through a lens 22 and strikes a detector 20 having a central detection zone 24 and a peripheral detection zone 26. If the source of light 12 is in proper focus on the skin, the quantity of light projected on the central detection zone 24 of the detector 20 and the quantity of light projected on the peripheral detection zone 26 of the detector 20 are within a pre-determined range. The boundary points of the range are preferably determined by trial and error. If the source of light 12 is not in proper focus on the skin, the quantity of light projected on the central detection zone 24 of the detector 20 and the quantity of light projected on the peripheral detection zone 26 of the detector 20 are not within the aforementioned pre-determined range. If the source of light 12 is not in proper focus on the skin, the lens 18 is maneuvered to place the source of light 12 in proper focus on the skin. When the source of light 12 is in proper focus on the skin, the source of light is driven at a sufficiently high level of power that the formation of an opening in the skin can occur.

Light from a source of light can also be used to align the source of light. In fact, it is preferred that the source of light be properly aligned prior to the adjustment of the focusing of the source of light. An opening in the skin can be formed with fewer of pulses of light if the source of light is aligned after each opening-forming pulse so that pulsed light from the source of light repeatedly strikes the same spot on the surface of the skin. If the source of light is not aligned after each opening-forming pulse, there is a high probability that a subsequent opening-forming pulse will miss the spot struck by the previous opening-forming pulse. The result of this hit-or-miss procedure will cause the source of light to emit a great many pulses before an opening is formed in the skin. There are several ways of carrying out the alignment aspect of the invention. In the preferred embodiments, a photosensitive dye is applied to the region of the skin at which the opening is to be formed by the pulses of light from the source of light. The interaction between the pulsed source of light and the photosensitive dye can be used to enhance the focusing and aligning of the source of light.

According to one embodiment, a change in reflectance of the photosensitive dye can be employed to indicate the spot at which a pulse of light has previously struck. The pulse of light, driven at a level of energy sufficiently high to form an opening or pore in the skin of a patient, upon striking the photosensitive layer, results in a photothermal change in the photosensitive dye. This change can result in a change in the reflectance of the dye, or in its decomposition, or in its removal from the skin. A scan over the general region of the skin with a light having a level of energy lower than that needed to form an opening in the skin can be used to identify the specific region of the skin that has been previously struck by a pulse of light. A change in reflectance of the previously struck region identifies the specific region that has been previously struck.

According to another embodiment, a change in the reflectance of a layer of reflective material coated over the photosensitive dye can be employed to indicate the spot at which a pulse of light has previously struck. The photosensitive dye is covered with a layer of reflective material. The reflective material can comprise, for example, a layer of dye, a thin polymeric film, a layer comprising a dye or pigment suspended in a polymer. A pulse of light, driven at a level of energy sufficiently high to form an opening or pore in the skin of a patient, upon striking the photosensitive layer, results in a change in the reflective layer, such as decomposition, melting, or ablation. A scan or read over the general region of the skin with a light having a level of energy lower than that needed to form an opening in the skin can be used to identify the specific region of the skin that has been previously struck. A change in reflectance of the previously struck region of the skin identifies the specific region that has been previously struck.

According to another embodiment, the fluorescent or luminescent properties of the photosensitive layer, or a secondary layer, can be used to identify the location of the region of the skin that has been previously struck by light. Upon being exposed to a pulse of light, driven at a level of energy sufficiently high to form an opening or pore in the skin of a patient, the fluorescent dye becomes photobleached. The region of the skin covered by the dye is no longer fluorescent, while the surrounding skin, which was not struck by light, remain fluorescent. A scan or read over the general region of the skin with a light having a level of energy lower than that needed to form an opening in the skin can be used to identify the specific region of the skin that has been struck by light by detecting changes in fluorescent intensity. In this embodiment, the semi-reflective mirror would be replaced by a dichroic filter.

According to another embodiment, the photothermal treatment of a receptor dye may result in a conformational change in the dye molecule, resulting in the demonstration of luminescence. A representative example of a suitable receptor dye is a thioindigo compound, which may be converted from a colorless cis form to a luminescent trans form, which can then be detected after illumination.

FIG. 3A illustrates how alignment can be adjusted. As shown in FIG. 3A, the upper right quadrant of the detector has more light falling on it than do the remaining quadrants. It would be relatively simple to determine the centroid of light intensity and from that value, the direction and magnitude that the lens 18 would have to be moved in order to align the light as desired. Alignment and focusing could be carried out at great enough speed such that the time between the aligning/focusing pulse and the operating (opening-forming) pulse would be so short as to minimize or eliminate improper focusing and alignment between operating pulses. The focusing/aligning operation can be used to cause light to either strike a particular spot on the skin or to avoid striking a particular spot on the skin.

Regardless of the approach used, the laser is intentionally defocused to encompass the previously formed spot. The spot appears to be brighter or darker than the surrounding skin. The blurry image is projected back on the detector (e.g., a four quadrant bulls-eye detector). By computing and analyzing the outputs of the detector segments, the magnitude and direction of misalignment can be determined.

Once alignment is optimized, then the lens 18 can be moved either toward or away from the skin to optimize the focus.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A method for forming an opening in the surface of the skin of a patient comprising the steps of:
    (1) projecting at least one pulse of light, driven at a level of energy that is not sufficient to form an opening in the skin of the patient, onto the surface of the skin of the patient;
    (2) collecting at least a portion of the light that is reflected from the skin of the patient;
    (3) projecting the collected, reflected light onto a detector to provide a signal;
    (4) adjusting the projection of the pulsed light onto the surface of the skin of the patient in such a manner that the signal projected onto the detector is optimized;
    (5) projecting at least one pulse of light onto the surface of the skin of the patient, wherein said pulse of light is driven at a level of energy that is sufficient to form an opening in the skin of the patient, whereby formation of an opening in the skin occurs, said at least one pulse of light in step (1) and said at least one pulse of light in step (5) being provided by the same source of light.

2. The method of claim 1, wherein the light is provided by a laser.

3. The method of claim 1, wherein the reflected light is collected by a lens.

4. The method of claim 1, wherein the detector is a bulls-eye detector.

5. The method of claim 1, wherein the detector is an array detector.

6. The method of claim 1, wherein the signal is optimized when the best focus has been attained.

7. The method of claim 1, wherein the signal is optimized when the best focus and the best alignment have been attained.

8. The method of claim 1, wherein the signal is optimized when the best alignment has been attained.

9. A method for forming an opening in the surface of the skin of a patient comprising the steps of:

(1) causing a pulsed beam of light, driven at a level of energy that is insufficient to form an opening in the skin of the patient, to pass through a lens to project a spot on the surface of the skin of the patient;

(2) causing light that is reflected from the surface of the skin to pass through a lens to project a spot on a target on a detector to provide a signal;

(3) moving the lens that projected a spot on the surface of the skin of a patient in such a direction that the quantity of the light reflected from the surface of the skin of the patient and projected on the target on the surface of the detector provides a signal that indicates the best alignment; and (4) causing a pulsed beam of light, driven at a level of energy at which an opening in the skin can be formed, to pass through a lens to project a spot on the surface of the skin of the patient, whereby formation of an opening in the skin occurs, said pulsed beam of light in step (1) and said pulsed beam of light in step (4) being provided by the same source of light.

10. The method of claim 9, wherein the light is provided by a laser.

11. The method of claim 9, wherein the reflected light is collected by a lens.

12. The method of claim 9, wherein the detector is a bulls-eye detector.

13. The method of claim 9, wherein the detector is an array detector.

14. The method of claim 9, wherein the signal is optimized when the best alignment has been attained.

15. A method for forming an opening in the surface of the skin of a patient comprising the steps of:

(1) causing a pulsed beam of light, driven at a level of energy that is insufficient to form an opening in the skin of the patient, to pass through a lens to project a spot on the surface of the skin of the patient;

(2) causing light that is reflected from the surface of the skin to pass through a lens to project a spot on a target on a detector to provide a signal;

(3) moving the lens that projected a spot on the surface of the skin of a patient in such a direction that the quantity of the light reflected from the surface of the skin of the patient and projected on the target on the surface of the detector provides a signal that indicates the best focus; and (4) causing a pulsed beam of light, driven at a level of energy at which an opening in the skin can be formed, to pass through a lens to project a spot on the surface of the skin of the patient, whereby formation of an opening in the skin occurs, said pulsed beam of light in step (1) and said pulsed beam of light in step (4) being provided by the same source of light.

16. The method of claim 15, wherein the light is provided by a laser.

17. The method of claim 15, wherein the reflected light is collected by a lens.

18. The method of claim 15, wherein the detector is a bulls-eye detector.

19. The method of claim 15, wherein the detector is an array detector.

20. The method of claim 15, wherein the signal is optimized when the best focus has been attained.

21. A method for forming an opening in the surface of the skin of a patient comprising the steps of:

(1) causing a pulsed beam of light, driven at a level of energy that is insufficient to form an opening in the skin of the patient, to pass through a lens to project a spot on the surface of the skin of a patient;

(2) causing light that is reflected from the surface of the skin of the patient to pass through a lens to project a spot on a target on the surface of a detector to provide a signal;

(3) moving the lens that projected the spot on the surface of the skin of the patient in such a direction that the quantity of the light reflected from the surface of the skin of the patient and projected on the target on the surface of the detector provides a signal that indicates the best alignment;

(4) moving the lens that projected the spot on the surface of the skin of the patient axially in such a direction that the quantity of the light reflected from the surface of the skin of the patient and projected on the target on the detector provides a signal that indicates the best focus; and (5) causing a pulsed beam of light, driven at a level of energy that is sufficient to form an opening in the skin of the patient, to pass through a lens to project a spot on the surface of the skin of the patient, whereby formation of an opening in the skin occurs, said pulsed beam of light in step (1) and said pulsed beam of light in step (5) being provided by the same source of light.

22. The method of claim 21, wherein the light is provided by a laser.

23. The method of claim 21, wherein the reflected light is collected by a lens.

24. The method of claim 21, wherein the detector is a bulls-eye detector.

25. The method of claim 21, wherein the detector is an array detector.

26. The method of claim 21, wherein the signal is optimized when the best focus and the best alignment have been attained.

* * * * *